United States Patent
Shao et al.

(10) Patent No.: US 9,920,387 B2
(45) Date of Patent: Mar. 20, 2018

(54) STRAIN OF MARINE OIL-DEGRADING BACTERIA, COMPOUNDS OBTAINED BY FERMENTATION AND THEIR APPLICATIONS

(71) Applicants: THIRD INSTITUTE OF OCEANOGRAPHY,STATE OCEANIC ADMINISTRATION, Xiamen (CN); CHINA OCEAN MINERAL RESOURCES RESEARCH AND DEVELOPMENT ASSOCIATION, Beijing (CN)

(72) Inventors: Zongze Shao, Xiamen (CN); Xiaoman Shi, Xiamen (CN); Wanpeng Wang, Xiamen (CN)

(73) Assignee: THIRD INSTITUTE OF OCEANOGRAPHY, STATE OCEANIC ADMINISTRATION, Xiamen (CN)

( * ) Notice: Subject to any disclaimer, the term of this patent is extended or adjusted under 35 U.S.C. 154(b) by 13 days.

(21) Appl. No.: 14/914,654

(22) PCT Filed: Feb. 6, 2015

(86) PCT No.: PCT/CN2015/072442
§ 371 (c)(1),
(2) Date: Feb. 26, 2016

(87) PCT Pub. No.: WO2016/011805
PCT Pub. Date: Jan. 28, 2016

(65) Prior Publication Data
US 2016/0289781 A1    Oct. 6, 2016

(30) Foreign Application Priority Data
Jul. 24, 2014    (CN) .......................... 2014 1 0354363

(51) Int. Cl.
| C12N 1/20 | (2006.01) |
| C12R 1/01 | (2006.01) |
| C02F 3/34 | (2006.01) |
| C07D 205/08 | (2006.01) |
| C12P 17/10 | (2006.01) |
| C12N 1/26 | (2006.01) |
| C02F 101/32 | (2006.01) |
| C02F 103/08 | (2006.01) |

(52) U.S. Cl.
CPC ................. *C12R 1/01* (2013.01); *C02F 3/34* (2013.01); *C02F 3/344* (2013.01); *C07D 205/08* (2013.01); *C12N 1/20* (2013.01); *C12N 1/26* (2013.01); *C12P 17/10* (2013.01); *C02F 2101/32* (2013.01); *C02F 2103/08* (2013.01)

(58) Field of Classification Search
None
See application file for complete search history.

(56) References Cited

U.S. PATENT DOCUMENTS

2009/0211345 A1*   8/2009   Nahm ................ G01N 21/6428
                                                                73/61.55

FOREIGN PATENT DOCUMENTS

| CN | 1900284 A | 1/2007 |
| CN | 1904033 A | 1/2007 |

OTHER PUBLICATIONS

Liu et al. Environmental Microbiol. (2011) 13(5): 1168-1178.*
definition of "emulsion" downloaded from http://www.dictionary.com/browse/emulsion on Jul. 22, 2017.*
Yuan, J. et al, "Genbank Accession No: EU603446.1", Genbank Database, Apr. 21, 2008, see sequence and relevant information.
Lai, Qiliang et al. "*Celeribacter indicus* sp. nov., a polycyclic aromatic hydrocarbon-degrading bacterium from deep-sea sediment and reclassification of huaishuia halophila as *Celeribacter halophilus* comb. nov.", International Journal of Systematic and Evolutionary Microbiology, vol. 64, No. Pt 12, Sep. 25, 2014, ISSN: online ISSN: 1466-5034, pp. 4161-4167, see whole document.
Lai, Qiliang et al, "Clone of alkane hydroxylase gene from a strain *Alcanivorax* sp. P40 isolated from deep sea of Indian ocean", Journal of Oceanography in Taiwan Strait, vol. 27, No. 2, May 31, 2008, ISSN: 2095-4972, pp. 141-146, see the whole document.
Liu Chenli and Shao Zongze. "*Alcanivorax dieselolei* sp. nov., a novel alkane-degrading bacteriumisolated from sea water and deep-sea sediment" International Journal of Systematic and Evolutionary Microbiology, vol. 3, No. 55, May 31, 2005, ISSN: 1466-5026, pp. 1181-1186, see the whole document.
N. Qiao and Z. Shao. "Isolation and characterization of a novel biosurfactant produced by hydrocarbon-degrading bacterium Alcanivorax dieselolei B-5" Journal of Applied Microbiology, vol. 108, No. 4, Apr. 30, 2010, ISSN 1365-2672, pp. 1207-1216, see the whole document.

* cited by examiner

Primary Examiner — Susan M Hanley
(74) Attorney, Agent, or Firm — Gokalp Bayramoglu

(57) ABSTRACT

A strain of marine oil degrading bacteria, compounds obtained by fermentation and their uses are published. The name is *Alcanivorax dieselolei* T6-6, with preservation Number: CGMCC NO: 9033. It belongs to γ-proteobacteria, oceanospirillales, alkane degrading bacteria branch, *alcanivorax* category and diesel *alcanivorax* species. The said bacteria can be used to degrade and remove petroleum hydrocarbon, control environmental pollution, produce surfactants, reduce surface tension of water, and for other purposes; a compound can be isolated from secondary metabolites after fermentation, one of which is *dieselolei* T6-6, 2-amino-6-(N-2-carbonyl-4-tridecyl-cyclobutane) hexanoic acid, and it is a kind of lysine ester. The compound has emulsifying activity on different organics, antibacterial effects against Gram-positive bacteria and fungus, and a better cytotoxic activity.

2 Claims, 10 Drawing Sheets

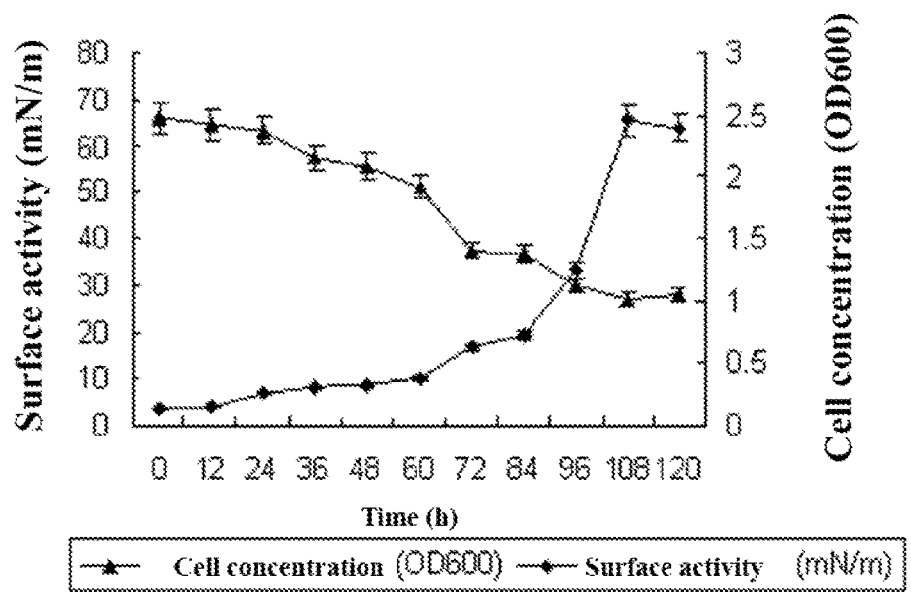
Fig. 3
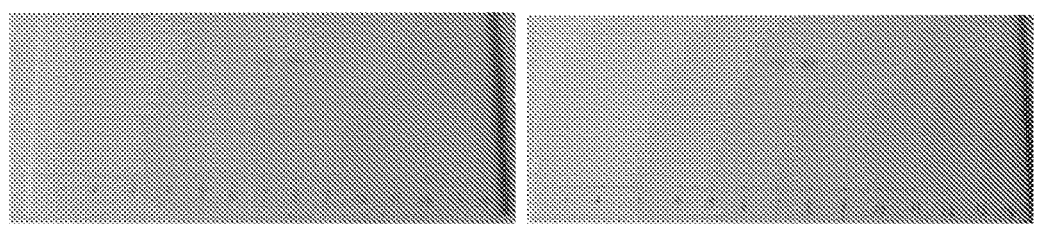
Fig. 4A                                Fig. 4B the hydrophobic layer of Strains Alcanivorax dieselolei T6-6
↓
Hexane extraction (mainly to remove less polar component n-hexadecane, fatty acids, etc.)
↙ ↘
water (28.5 mNm⁻¹), the organic phase
↓
Chloroform: methanol=1:1 (Volume ratio) Extraction (Concentrated to dryness, take a little and dissolved in water, surface tension is 28.8 mNm⁻¹)
↙ ↘
the organic phase (27.8 mNm⁻¹), cell pellet (62.3 mNm⁻¹)

the supernatant of strains Alcanivorax dieselolei T6-6
↓
Precipitated with acid (With concentrated hydrochloric acid make the pH was adjusted to 2.0)
↓
4℃, 10000r/min Centrifugal 20min, take some cell pellet, Lyophilized, Chloroform: methanol=1:1 (Volume ratio) Extraction
↙ ↘
the organic phase (28.1 mNm⁻¹), cell pellet (65.2 mNm⁻¹)

Fig. 15

STRAIN OF MARINE OIL-DEGRADING BACTERIA, COMPOUNDS OBTAINED BY FERMENTATION AND THEIR APPLICATIONS

BACKGROUND OF THE INVENTION

The present invention relates to the field of microorganism, in particular to a strain of marine oil-degrading bacteria and its application.

Marine microorganism is the generic name of ocean lower organisms in the ocean with small size and simple structure, including bacteria, fungus, actinomycetes, mould, yeast, viruses, *chlamydia, mycoplasma*, phages, micro algae and tiny protozoans, etc. Before the 1990s, there were few chemical researches and reports on secondary metabolites of marine microorganisms, and the hot topic had been terrestrial fungal resources; after 1990s, chemical researches and reports on secondary metabolites of marine microorganisms significantly increased; The largest number of new compounds were found in 1998 and 2000, and the number of new compounds derived from marine microorganisms also increases. Many compounds have new skeletons, indicating that marine microorganisms have unique metabolic and physiological mechanisms, and are the potential rich resource for new compounds and drug lead compounds.

*Alcanivorax* is an important alkane degrading bacteria in marine oil pollution environment. Currently, this kind of bacteria has been separated out or detected in surface seawater or in deep-sea sediments around the world. Six genera have been reported, the first one is *Alcanivorax borkumensis* SK2, which was obtained through separation by Yakimov et al in 1998, and can produce glycolipids surface active agent and glucose lipids (one anhydroglucose unit links four 3-OH fatty acid); *Alcanivorax dieselolei* B-5 separated from surface seawater of Yellow Seacan reduce fermentation broth surface tension to less than 30 mm/m, in the induction medium with cetane as the only carbon source, and is identified as proline lipid (hexadecanoic acid and proline lipid can be dehydrated and condensed to a linear lipid peptide.) Biosurfactant is the metabolites generally produced by microorganisms (especially some fungus and bacteria) under certain culture conditions, including glycolipids, lecithin, polysaccharide compounds, lipoprotein-lipid polypeptides, hydroxyl compound and cross linking fatty acids, etc. Non-polar hydrophilic group of biosurfactant is generally long chain fatty acid or beta hydroxy fatty acid, alpha-alkyl-beta hydroxy fatty acid; while polar hydrophilic group has various types, such as carbohydrate, amino acids, cyclic peptides, phosphates, alcohols, etc., and they generally have batter performance of lowering surface tension and interfacial tension.

Biosurfactant has some unique characteristics that common synthetic surfactants do not have: generally features lower critical micelle concentration, less dosage and high efficiency; and is biodegradable, non-toxic, and environmentally friendly; They can be used in the fields of environmental protection, cosmetics, drugs and food additives; with stable chemical structures and property, biosurfactants can be used in some extreme environments such as high temperature, high salt, and high pH, etc.; Biosurfactants can be classified intoglycolipid, lipopeptide, lipoprotein, phospholipid, fatty acid, polymeric surfactant and granular surfactant. The hydrophilic group of lipopeptide biosurfactant is composed of oligopeptide or amino acids, while the hydrophobic group consists of fatty acids, and the lipopeptide is usually a mixture formed by a variety of heterogeneous monomers. The chain length of fatty acid in the lipopeptide, the number of branched chains and composition of amino acid are so variable that the lipopeptide biosurfactant is in a great variety, the representative of which includes surfactin, lichenysin, fengycin, iturin, mycosubtilin, and bacillomycin, etc. The lipopeptides currently found mainly belong to family *Bacillus*, such as *B. subitilis. B. circulans, B. cereus, B. polymyxa, B. mesentericus* and the like. In addition to *Bacillus*, some other microorganisms, including *mycobacterium fortuirum, Streptomyces canus, Pseudomonas fluorescens,* and *serratiamarcescens*, etc., also produce lipopeptides.

TABLE 1 several important microbial surfactants source and their characteristics

| lipopeptides | Microbiological | liquid surface tension (mN/m) | CMC | Interfacial tension (mN/m) |
| --- | --- | --- | --- | --- |
| Peptide-lipid | *B. licheniformis* | 27 | 12-20 | 0.1-0.3 |
| Serrawettin | *S. marcescens* | 28-33 | / | / |
| Viscosin | *P. fluorescens* | 26.5 | 150 | / |
| Surfactin | *B. subtilis* | 27-32 | 23-160 | 1 |

BRIEF SUMMARY OF THE INVENTION

The present invention aims to provide a marine oil-degrading bacteria strain *Alcanivorax dieselolei* T6-6.

For the aforementioned purpose, the present invention provides a marine oil-degrading bacteria strain *Alcanivorax dieselolei* T6-6 with the preservation No: CGMCC 9033.

The preparation method of A marine oil degrading bacteria *Alcanivorax dieselolei* T6-6 following steps:

Take deep sea water of southwest Indian Ocean collected at the $20^{th}$ voyage into conical flask, which is kept at 121° C., for 20 minutes, adding pre-autoclavable mixture of crude oil and diesel fuel (at concentration of 4.2 $g/dm^3$) at a ratio of 1:1; Preferably, the deep sea water of 50 $cm^3$ is added with 0.21 g crude oil and diesel fuel mixture, pre-autoclavable $NH_4NO_3$ (at final concentration of 1 $g/dm^3$, pH=7.5), KH2PO4 solution (at final concentration of 1 $g/dm^3$) and $FeSO_4$ solution (at final concentration of 0.4 $\mu g/dm^3$ and being treated by 0.22 μm membrane filtration sterilization); take 50 $cm^3$ deep sea water into the flask, which is kept under 28° C. and dark cultured in a shaker at 160 r/min; after being cultured for 6 days, black oil contamination disappears, and then take 2 $cm^3$ of above solution to the same medium, after transferring for 5 times, the enrichment is gradient diluted, and then applied on a 2216 L flat; the solid plate is added with 1.5% agar, and strains stated in Claim 1 are obtained after isolating single bacterium.

The present invention also protects applications of *Alcanivorax dieselolei* T6-6 The stated strains can be used to degrade and remove petroleum hydrocarbon; and the method for the stated strains to degrade and remove petroleum hydrocarbon.

The stated strains can be used for the production of biosurfactant; and the usage of the stated strains to produce biosurfactant.

The stated strains can be used to lower surface tension of water; and the method for the stated strains to lower surface tension of water The *Alcanivorax dieselolei* T6-6 can produce a kind of compound by fermentation, which is characterized in that the structural formula of this compound is as follows,

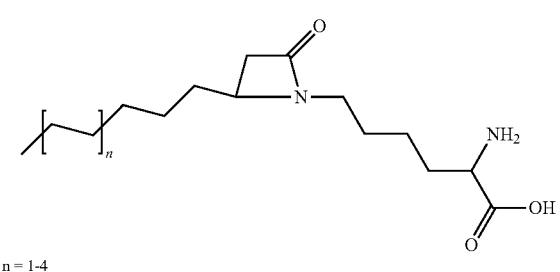

n = 1-4

When n=1, the molecular formula is $C_{18}H_{34}N_2O_3$ with molecular weight of 326, and it is named as 2-amino-6-(N-2-carbonyl-4-nonyl-cyclobutane) hexanoic acid; when n=2, the formula is $C_{20}H_{38}N_2O_3$ with molecular weight of 354, and it is named as 2-amino-6-(N-2-carbonyl-4-undecyl-cyclobutane) hexanoic acid; when n=3, the molecular formula is $C_{22}H_{42}N_2O_3$ with molecular weight of 382, and it is named as 2-amino-6-(N-2-carbonyl-4-tridecyl-cyclobutane) hexanoic acid and also called lysine aliphatic *dieselolei* T6-6; when n=4, the molecular formula is $C_{24}H_{46}N_2O_3$ with molecular weight of 410, and it is named as 2-amino-6-(N-2-carbonyl-4-pentadecyl-cyclobutane) hexanoic acid.

The said compound, the lysine ester *dieselolei* T6-6 with the molecular formula $C_{22}H_{42}N_2O_3$, is prepared by fermenting the strain, and its structural formula is provided as follows.

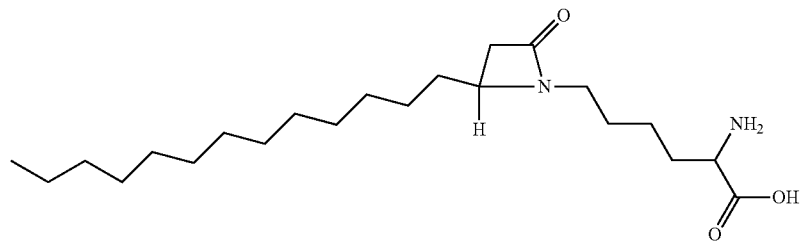 [SMILES: CCCCCCCCCCCCCC1CC(=O)N1CCCCC(N)C(=O)O]

The stated lysine ester *dieselolei* T6-6 can be used to emulsify organic matters and inhibit Gram-positive bacteria, as well as used for bacteriostasis against fungus; and the method by which the stated lysine ester *dieselolei* T6-6 is used to emulsify organic matters and inhibit Gram-positive bacteria, as well as used for bacteriostasis against fungus.

The strain *Alcanivorax dieselolei* T6-6 and the strain *Alcanivorax dieselolei* B-5 (AY683537) have alkane degrading ability and liquid surface tension reducing ability. The strain *A. dieselolei* B-5 now has been identified as a type strain of *dieselolei* of the family *Alcanivorax*, with the preservation No. 1A00001 in MCCC (Marine Culture Collection of China). The strain *A. dieselolei* B-5 has diesel and alkane degrading ability, grows well in MSM medium with Hexadecane as the sole carbon source, can reduce surface tension of fermentation liquid to 31 mN m-1 or so and is one of the strains capable of producing surfactant. The method has been detailed in a document (Liu C and Shao Z.

*Alcanivorax dieselolei* sp. nov., a novel alkane-degrading bacterium isolated from sea water and deep-sea sediment [J]. Int J Syst Evol Microbiol, 2005, 55, 1181-1186).

The strain *Alcanivorax dieselolei* T6-6 is alkane degradative bacteria isolated and screened from abyssal sediment samples (collected from Southwest Indian Ocean in the applicant's 20th voyage for oceanic research). The strain *Alcanivorax dieselolei* T6-6 can be used to degrade petroleum and alkane and to degrade and remove petroleum hydrocarbon.

*Alcanivorax dieselolei* T6-6 has high cell hydrophobicity, and with the higher affinity of petroleum material than the control strain.

The chemical composition of the main surfactant produced by the strain *Alcanivorax dieselolei* T6-6 is lysine ester which is lipopeptide generated by reaction of beta-hydroxy-hexadecanoic acid and lysine. The lysine ester has simple structure and can be chemically synthesized by one-step esterification reaction.

*Alcanivorax dieselolei* T6-6 produced a surfactant of lysine, it can reduce surface tension to 26-28 mN m-1 or so, CMC value (32 mg 1-1).

*Alcanivorax dieselolei* T6-6 produced Lysine lipid has well thermal stability.

*Alcanivorax dieselolei* T6-6 produced Lysine lipid holds high surface activity.

*Alcanivorax dieselolei* T6-6 produced Lysine lipid having excellent emulsifying ability.

*Alcanivorax dieselolei* T6-6 produces lysine lipid can Inhibit Gram-positive bacteria and fungus

*Alcanivorax dieselolei* T6-6 can be used as strains to producing surfactants.

*Alcairivorax dieselolei* T6-6 strain, an alkane degrading bacteria, was isolated on the 20th voyage in the Southwest Indian Ocean from deep-sea sediments. It was deposited under the Budapest Treaty in the Chinese Type Culture Collection with the accession number: CGMCC NO: 9033 on Apr. 9, 2014. The address of the depository is Microbiology Research Institute of China Science Academy, No. 3 Courtyard No. 1 Beichen West Road, Chaoyang district Beijing China.

16S rDNA of the strain *Alcanivorax dieselolei* T6-6 is sequenced (by Invitrogen (Shanghai) Ltd.) and compared by NCBI (National Center of Biotechnology Information). It is found that the strain *Alcanivorax dieselolei* B-5 (AY683537) has the highest similarity to the strain *Alcanivorax dieselolei* T6-6, up to 99.866%. The *Alcanivorax dieselolei* T6-6 belongs to γ-proteobacteria, oceanospirillales, alkane degrading bacteria branch, *Alcanivorax* category and diesel *Alcanivorax* species.

16S rDNA phylogenetic tree of *Alcanivorax dieselolei* T6-6 shown in FIG. 1.

16S rRNA sequence of *Alcanivorax dieseloleiT6-6*, SEQ ID NO: 1,

| | |
|---|---|
| GATCAGAGTTTGATCCTGGCTCAGATTGAACGCTGGCGGCAGGCCTAACACATGCAAGTC | 60 |
| GAGCGGAAACGATGGGAGCTTGCTCCCAGGCGTCGAGCGGCGGACGGGTGAGTAACACGT | 120 |
| GGGAATCTGCCCATTAGTGGGGGATAACTCGGGGAAACTCGAGCTAATACCGCATAATCC | 180 |
| CTACGGGGGAAAGCAGGGGATCTTCGGACCTTGCGCTGATGGATGAGCCCGCGTCGGATT | 240 |
| AGCTTGTTGGTGGGGTAATGGCCCACCAAGGCGACGATCCGTAACTGGTCTGAGAGGATG | 300 |
| GCCAGTCACACCGGGACTGAGACACGGCCCGGACTCCTACGGGAGGCAGCAGTGGGGAAT | 360 |
| CTTGGACAATGGGCGCAAGCCTGATCCAGCCATGCCGCGTGTGTGAAGAAGGCCTTCGGG | 420 |
| TTGTAAAGCACTTTCAGTAGGGAGGAAGGCTTTGGGCTAATACCCTGGAGTACTTGACGT | 480 |
| TACCTACAGAAGAAGCACCGGCTAATTTCGTGCCAGCAGCCGCGGTAATACGAAAGGTGC | 540 |
| GAGCGTTAATCGGAATTACTGGGCGTAAAGCGCGCGTAGGCGGTGTGTTAAGTCGGATGT | 600 |
| GAAAGCCCAGGGCTCAACCTTGGAATTGCATCCGATACTGGCACGCTAGAGTGCAGTAGA | 660 |
| GGGAGGTGGAATTTCCGGTGTAGCGGTGAAATGCGTAGAGATCGGAAGGAACACCAGTGG | 720 |
| CGAAGGCGGCCTCCTGGACTGACACTGACGCTGAGGTGCGAAAGCGTGGGGAGCAAACAG | 780 |
| GATTAGATACCCTGGTAGTCCACGCCGTAAACGATGTCTACTAGCCGTTGGGGTCCTTAG | 840 |
| TGACTTTGGTGGCGCAGCTAACGCGATAAGTAGACCGCCTGGGGAGTACGGCCGCAAGGT | 900 |
| TAAAACTCAAATGAATTGACGGGGGCCCGCACAAGCGGTGGAGCATGTGGTTTAATTCGA | 960 |
| TGCAACGCGAAGAACCTTACCAGGCCTTGACATCCTGCGAACTTTCTAGAGATAGATTGG | 1020 |
| TGCCTTCGGGAGCGCAGTGACAGGTGCTGCATGGCTGTCGTCAGCTCGTGTCGTGAGATG | 1080 |
| TTGGGTTAAGTCCCGTAACGAGCGCAACCCTTGTCCTTAGTTGCCAGCACTTCGGGTGGG | 1140 |
| AACTCTAGGGAGACTGCCGGTGACAAACCGGAGGAAGGTGGGGACGACGTCAAGTCATCA | 1200 |
| TGGCCCTTACGGCCTGGGCTACACACGTGCTACAATGGTTGGTACAGAGGGTTGCGAAGT | 1260 |
| CGCGAGGCGGAGCTAATCTCTCAAAGCCAATCGTAGTCCGGATTGGAGTCTGCAACTCGA | 1320 |
| CTCCATGAAGTCGGAATCGCTAGTAATCGCGGATCAGAATGCCGCGGTGAATACGTTCCC | 1380 |
| GGGCCTTGTACACACCGCCCGTCACACCATGGGAGTGGATTGCACCAGAAGTAGTTAGTC | 1440 |
| TAACCTTCGGGAGGACGATTACCACGGTGTGGTTCATGACTGGGGTGAAGTCGTAACAAG | 1500 |
| GTAGCCGTAA | |

BRIEF DESCRIPTION OF THE DRAWINGS

FIG. 3 is Relationship between cell growth and biosurfactant production during the growth of strain T6-6.

FIG. 4 is TLC analysis of biosurfactants from strain T6-6 (4A) Iodine vapor as developer and (4B) ninhydrin as developer.

FIG. 15 is a process of crude extract.

DETAILED DESCRIPTION OF THE INVENTION

Figure 1:
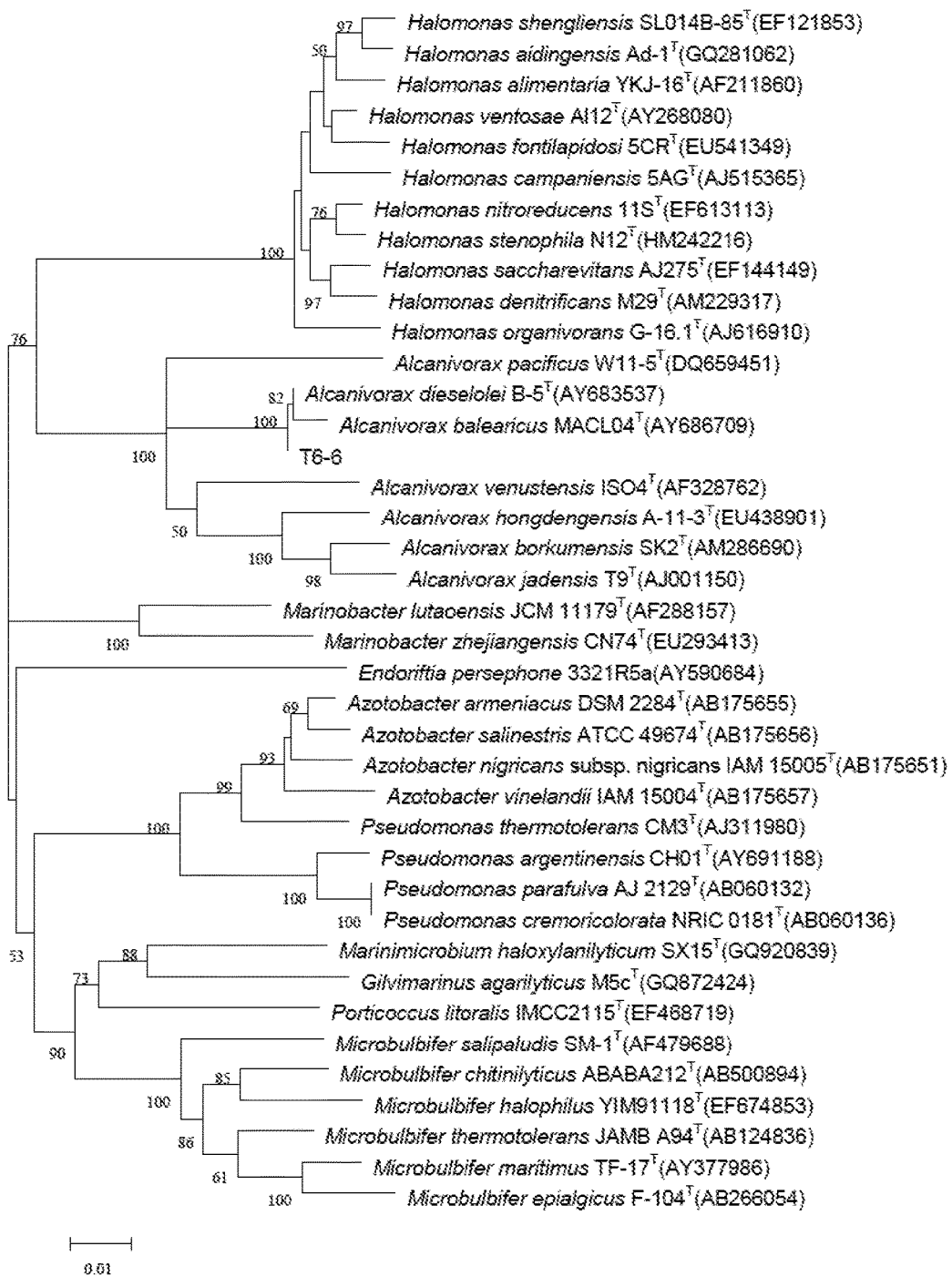
FIG. 1 is Phylogenetic tree based on 16s rDNA nucleotide sequence of T6-6

The following content is the detailed description of present embodiment. The example of said embodiment is shown in figures; furthermore, the same or similar label all along indicates the same or similar elements or the elements with same or similar functions. Following embodiment that is described with reference to figures is exemplary, and is intended for the explanation of this invention and shall not be interpreted as limiting the invention. Where there is without indication of specific technology or conditions in embodiment, the operation shall be handled in accordance with the technical or conditions described in the literature of this field, or with the product manual. If the used reagent or equipment is not marked with manufacturer, they can be purchased from the market.

Embodiment 1: Isolation and Culture of Strains

Isolation method: Take 50 cm$^3$ deep sea water (collected from southwest Indian Ocean at the 20$^{th}$ voyage) into a 250 cm$^3$ conical flask, which is kept at 121° C. for 20 minutes, add 0.21 g pre-autoclavable mixture of crude oil and diesel fuel at a mass ratio of 1:1; add pre-autoclavable NH$_4$NO$_3$ (at final concentration of 1 g/dm$^3$), KH2PO4 solution (pH=7.5; at final concentration of 1 g/dm$^3$) and FeSO$_4$ solution (at final concentration of 0.4 μg/dm$^3$ and being treated by 0.22 μm membrane filtration sterilization); take 50 cm$^3$ above deep sea water into above flask, which is kept at 28° C. and dark cultured in a shaker at 160 r/min; after being cultured for 6 days, black oil contamination disappears, and then take and transfer 2 cm$^3$ of above solution to the same medium, after transferring for 5 times, the enrichment is gradient diluted and applied on a 2216 L flat (2216 L medium: NaAc: 1 g, yeast powder: 2 g, tryptone: 10 g, sodium lemon: 0.5 g, being dissolved in 1 dm$^3$ aged seawater, adjust pH to 7.5. Add 1.5% AGAR powder to solid plate) to isolate single bacterium.

Finally, a strain isolated from a fungal strain, the strain was named as: T6-6, i.e. the identification *dieselolei* T6-6 *Alcanivorax* strain (A) Form The method: inoculate the strain onto a 2216 L plate, which is cultured in darkness at the temperature of 20° C. for ten days; measure the diameter of the bacterial colony and record color of the bacterial colony. The *Alcanivorax dieselolei* T6-6 is Gram-negative bacteria and is positive in oxidase and catalase and capable of reducing nitrate but not nitrite. When the strain grows on the 2216 L plate, the bacterial colony formed is small and milk white, has translucent edges, smooth surface, central bumps and regular exterior, has no halos and is rod-shaped under oil lenses.

(B) Colony PCR and 16s rDNA Sequences

The PCR (polymerase chain reaction) method of the bacterial colony: DNA extraction of the *Alcanivorax dieselolei* T6-6 and amplification of 16S rDNA are carried out according to a document (Liu C, Shao Z. *Alcanivorax dieselolei* sp. nov., a novel alkane-degrading bacterium isolated from sea water and deep-sea sediment [J]. International Journal of Systematic and Evolutionary Microbiology, 2006, 55:1181~1186). PCR amplification of 16S rDNA is performed with the aid of a primer SEQ ID NO.2-3.

```
SEQ ID NO: 1:
16SF:
5'-AGAGTTTGATCCTGGCTCAT-3'  i.e., SEQ ID NO: 2;

16SR:
5'-ACGGCTACCTTGTTACGACT-3' i.e., SEQ ID NO: 3;
```

The target fragment size is about 1500 bp. The primer used for PCR is synthesized by TaKaRa. The PCR reaction system (5.0 mm$^3$ in total volume): 10*buffer 5.0 mm$^3$, dNTP (0.2 mmol/dm) 4.0 mm$^3$, 16SR (10 pmol/dm$^3$) 1.0 mm$^3$, 16SF (10 pmol/dm$^3$) 1.0 mm$^3$, Taq enzyme (2 U/mm$^3$) 0.4 mm$^3$, DNA template (50 ng~1 μg) 1.0 mm$^3$ and 37.4 mm$^3$ of deionized water. Conditions of PCR amplification: 95° C. for 5 minutes, 95° C. for 1 minute, 55° C. for 1 minute and 72° C. for 2 minutes for 30 cycles and 72° C. for 5 minutes. Products of PCR amplification are converted into *E. coli* DH5alpha competent cells and sequenced by Sangon Biotech (Shanghai) Co., Ltd after being purified and connected with pMD19-T. The sequencing result is analyzed by the NCBI (http://www.ncbi.nlm.nih.gov/BLAST), sequences of sibling species in the amplification sequence and the GenBank are compared via software DNAMA (version 5.1) and the phylogenetic tree is drawn by using MEGA3.1.

Take oil and diesel oil mixture as the carbon source for enrichment culture; the strain of *Alcanivorax dieselolei* T6-6 is isolated from sediment samples of southwest Indian Ocean collected at the 20th voyage, and it has obvious diesel degradation ability; single bacterium validation showed that 4.2 g/dm$^3$ diesel oil can be emulsified and mostly degraded after being cultured for 3 days; only a small part of emulsified oil droplets are left on the surface, which may be non-alkane component in diesel oil. The strain was determined, and has been preserved in Chinese Type Culture Collection since Apr. 9, 2014, with its Preservation Numbers: CGMCC NO: 9033.

In this study, the amplified 16S rDNA on Genebank registration number as shown in FIG. 1 phylogenetic tree.

The type analysis of the *Alcanivorax dieselolei* T6-6 and sequence analysis of 16S rDNA demonstrate that the *Alcanivorax dieselolei* T6-6 belongs to γ-proteobacteria, oceanospirillales, alkane degrading bacteria branch, *Alcanivorax* category and diesel *Alcanivorax* species. The 16S rDNA phylogenetic tree is shown as FIG. 1.

Embodiment 2: Test of Alkane Degradation Ability of *Alcanivorax Dieselolei* T6-6

Test method of alkane degradation rate: Scrape *Alcanivorax dieselolei* T6-6 from the fresh flatin to a sterile EP tube added with MMC medium (formula: NaCl 24 g/l, MgSO$_4$ 7H$_2$O: 7.0 g/l, NH$_4$NO$_3$: 1.0 g/l, KCl: 0.7 g/l, KH$_2$PO$_4$: 2.0 g/l Na$_2$HPO$_4$: 3.0 g/l, PH=7.4, 1 L distilled water, with appropriate amount of 0.22 um membrane filter sterilized trace elements mixture added after sterilization (CaCl$_2$ 2 mg/l; FeC$_1$.6H$_2$O, 50 mg/l; CuSO$_4$, 0.5 mg/l; MnCl$_2$.4H$_2$O, 0.5 mg/l; ZnSO$_4$.7H$_2$O, 10 mg/l); after mixing, add a certain concentration of bacteria into a 150 ml conical flask added with 50 ml MMC medium (two parallel controls are provided for each alkane), add 1% alkane $C_{12}$, $C_{14}$, $C_{16}$ and $C_{18}$ into MMC liquid medium for culture observation. Alkane degradation rate (%)=(I-residual amount in the fermented liquid/blank control)×100%; draw standard curve according to 2 ul, 1 ul, 0.5 ul, 0.25 ul and 0.125 ul internal chlorinated dodecane, and take the one added with C12, C14, C16 and C18 but without *Alcanivorax dieselolei* T6-6 as the blank control. Add 9 ml n-hexane into a fermentation bottle, shaking by table concentrator at 180 r/min for 30 minutes, standing for stratification, and take the sublayer as n-hexane phase. Take a 10 ml volumetric flask to make a constant volume of 10 ml, use part of sample for dilution to 10$^{-9}$, and this sample is used for GC-MS. At the same time, make corresponding standard curves of C12, C14, C16 and C18, calculate alkane degradation rate, and the results obtained are shown in Table 2.

Figure 2A:
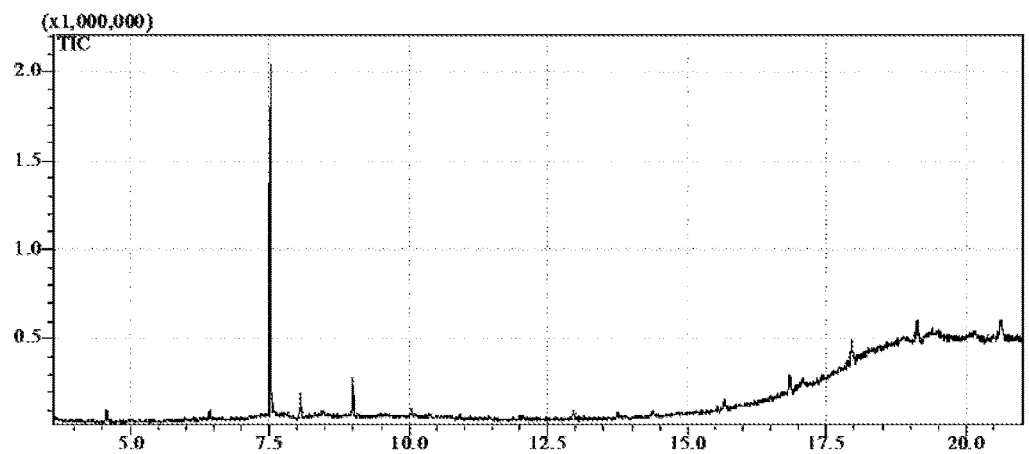
FIG. 2A and FIG. 2B are alkane biodegradation rate GC-MS spectras of strain *Alcanivorax dieselolei* T6-6. 2A is a C16 biodegradation rate of GC-MS specta. 2B is a C14 biodegradation rate of GC-MS specta.
Figure 2B:
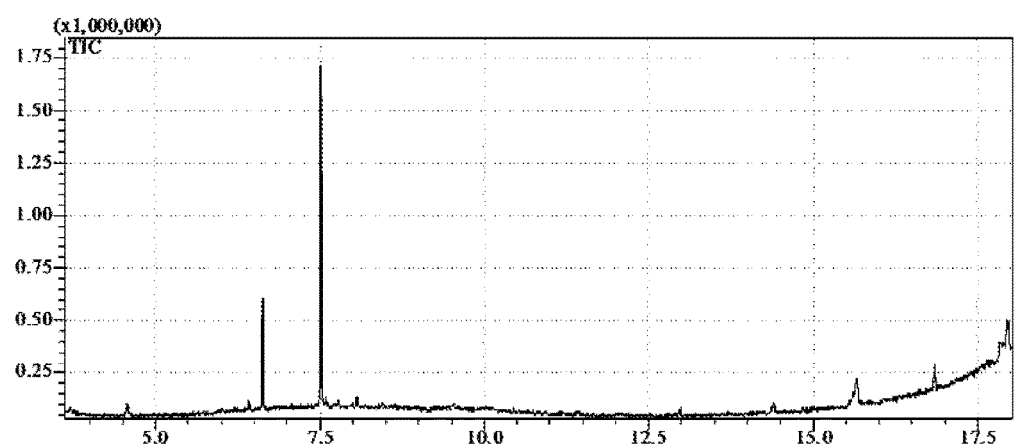

The *Alcanivorax dieselolei* T6-6 can utilize the straight-chain paraffins of $C_{10}$-$C_{36}$, with better degradation effect on the $C_{18}$ and its following alkanes so that $C_{12}$, $C_{14}$, $C_{16}$ and $C_{18}$ are used for determining degradation rate of the *Alcanivorax dieselolei* T6-6. The GC-MS analysis result indicates that degradation rate of $C_{16}$ is highest, at 92.3%, the degradation rates of the rest three are close, at about 50%. Details are shown in Table 2 and FIGS. 2A and 2B.

TABLE 2

Strain *Alcanivorax dieselolei* T6-6 alkane degradation rate and cell growth table

| alkane | degradation rate (%) | $OD_{600}$ |
|---|---|---|
| $C_{12}$alkane | 57.46 ± 2.5 | 1.62 ± 0.06 |
| $C_{14}$alkane | 50.28 ± 0.6 | 1.55 ± 0.05 |
| $C_{16}$alkane | 92.03 ± 0.5 | 2.69 ± 0.02 |
| $C_{18}$alkane | 46.62 ± 0.9 | 1.53 ± 0.05 |

"±" indicates three experimental error under the same experimental conditions, *Alcanivorax dieselolei* B-5 (AY683537) has alkane degradation too.

Embodiment 3: Test of Cell Surface Hydrophobicity of *Alcanivorax dieselolei* T6-6

Wash the fermentation liquid of strain *Alcanivorax dieselolei* T6-6 using phosphate buffer (pH 7.0) at a volume of 1:1, centrifuge it at room temperature (12000 RPM, 3 minutes) and collect bacteria. Repeat washing for three times, and finally have the cells suspended in 4 ml phosphate buffer, adjust the ultraviolet-visible spectrophotometer A600=0.5 or so, with the specific value measured as $A_0$. And then, divide the measured $A_0$ samples into 6 groups, add 1 ml of hydrophobic material crude oil, is-xylene, n-hexadecane, octadecane, mineral oil and liquid paraffin respectively. Shake the samples for 2 minutes using a oscillator, and stratifies them after by-standing for 30 minutes. Insert a syringe needle into the lower layer to draw 2 ml liquid, and measure its A value with a spectrophotometer, and record the value as A1. The strength of cell surface hydrophobicity can be calculated with the formula: $H\% = (A_0 - A_1)/A_0 \times 100$. The higher the H value is, the bigger the cell surface hydrophobicity. A comparison was conducted with the cell surface hydrophobicity of a *Myroides* sp. SM1 that has been reported, and the results show that *Alcanivorax dieselolei* T6-6 has a good cellular surface hydrophobicity against most organic materials (except liquid paraffin), and has a higher bacterial hydrophobicity than *Myroides* sp. SM1. The results shown in Table 3.

TABLE 3

Determination of the hydrophobicity of the surface of the strain *Alcanivorax dieselolei* T6-6 in the cell (%)

| Drain water content (hydrocarbon) | *Myroides* sp. SM1 | T6-6 |
|---|---|---|
| Crude oil | 85.48 | 68.88 ± 1.2 |
| the - xylene, | 28.07 | 32.24 ± 0.5 |
| n-hexadecane | 14.62 | 62.61 ± 0.8 |
| octadecane | 0.13 | 78.52 ± 1.5 |
| mineral oil | 3.78 | 72.45 ± 1.2 |
| liquid paraffin | 5.23 | 7.66 ± 0.8 |

NOTE:
the data of *Myroides* sp. SM1 from Songklanakarin J. Sci Technol, 2007, 29 (3): 769-779
"±" indicates three experimental error Embodiment 4: Analysis on Relationship Between Cell Growth of Strain *Alcanivorax dieselolei* T6-6 and Surface Tension Test method of liquid surface tension: Inoculate the *Alcanivorax dieselolei* T6-6 single bacterium into MSM medium on clean workbench (with 2% n-hexadecane as the sole carbon source), and culture it in constant temperature air bath shaker incubator (28° C., 200 rpm/min) until thalli obviously grow (about 3 to 5 days), during which take out 10 ml fermentation liquid every 24 hours, and measure its surface tension values using automatic interfacial tensiometer (Manufacturer: Chengde Precision Testing Machine Co., Ltd; Model: JZ-200-a automatic interface tensiometer). Put 10 ml fermented liquid of *Alcanivorax dieselolei* T6-6 into a measuring cup, the outer wall of which should be wiped dry, and then place the measuring cup on the operating platform of surface tension meter. Wash the suspension loop with pure water for several times in advance and rinse it with petroleum ether, acetone, then blow it to quickly volatilize acetone solution attached on its surface, finally place it on the operating platform to measurement. Before measurement, pay attention to the ambient temperature that is generally kept at 25° C. or so. (For refrigeration of supernatant and hydrophobic layer stratified after centrifugation, the surface tension should be measured when it gets to the room temperature. Thus, the result is comparability and credibility). When measuring liquid surface tension, pour 10 ml fermentation liquid of *A. dieselolei* T6-6 at temperature of 25° C. into a weighing cup, place the weighing cup in the center of the tray, press "▲" to make the platinum ring deep into 5 mm to 7 mm in the liquid, press "●" to stop; if the peak needs to be kept, firstly press "peak" button, and then press "▼", the display value will increase gradually, and finally stay at the maximum; this maximum value is the actually measured value of surface tension of liquid, and then press "●" to stop, after the maximum value is recorded, press "reset" button. Conduct gradient dilution and isolation of HLB flat (NaCl 3%) for the enrichment liquid with surface tension less than 40 mN m$^{-1}$ and obvious oil drainage activity, to obtain pure culture and analyze the single bacterial surface activity.

Hexadecane as the sole carbon source in the medium MSM (formula: (NH4)2SO4=1 g; KCl=0.11 g; NaCl=0.11 g; FeSO4.7H2O=2.8×10-5 g; anhydrous KH2PO4=0.34 g; K2HPO4.13H2O=0.44 g; MgSO4.7H2O=0.05 g; yeast extract=0.05 g; trace element solution 0.5 mL; hexadecane 2 mL, pH 7.4), 28° C., 150 rpm/min, cultured for 3-5 days.

Trace element solution (%): ZnSO4.7H2O=0.029 g; CaCl2=0.024 g; CuSO4=0.025 g; MnSO4.H2O=0.017 g.

For the fermented the strain *Alcanivorax dieselolei* T6-6, determine surface tension and $OD_{600}$ value of the fermentation liquid every 12 hours in 120 hours. The results show that active substances in the fermentation products of the *Alcanivorax dieselolei* T6-6 are mainly generated in a logarithmic phase of strain growth and the surface tension is the lowest at 26.0 mNm$^{-1}$ in a stable period. The results are shown in FIG. 3.

The strain *A. dieselolei* B-5 (AY683537) grows well in MSM medium with Hexadecane as sole carbon source and can reduce surface tension of the fermentation liquid to 31 mNm-1 or so. The method is the same as description above.

Embodiment 5: Isolation and Purification of Fermentation Products of Strain *Alcanivorax dieselolei* T6-6

After culturing MSM liquid medium (with 2% n-hexadecane as the sole carbon source, other ingredients are shown in Example 2) of strain *Alcanivorax dieselolei* T6-6 for 5 days, the surface tension of fermentation liquid is about 27 mNm$^{-1}$. After centrifugation at 12000 rpm and 4° C. for 20 minutes, the fermentation liquid is divided into three layers from top to bottom: white hydrophobic layer, supernatant and cell sediment. Determination results of the surface tension of these three layers: hydrophobic layer is 27.2 mNm$^{-1}$; supernatant is 31.3 mNm$^{-1}$; cell sediment is 59.2 mNm$^{-1}$. It can be seen that surface active substances produced by strain *Alcanivorax dieselolei* T6-6 are mainly in hydrophobic layer and supernatant. Crude extract are shown as FIG. 15.

Figure 5A:
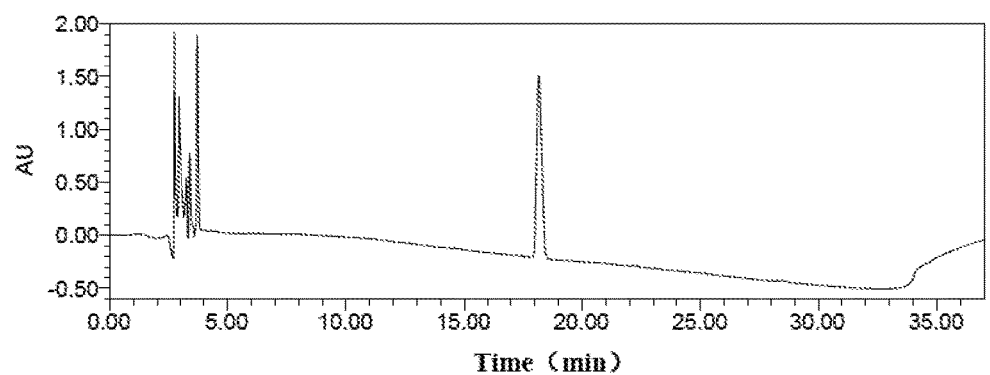
FIG. 5A is HPLC (210 nm peak) analysis of the compound dieselolein T6-6.
Figure 5B:
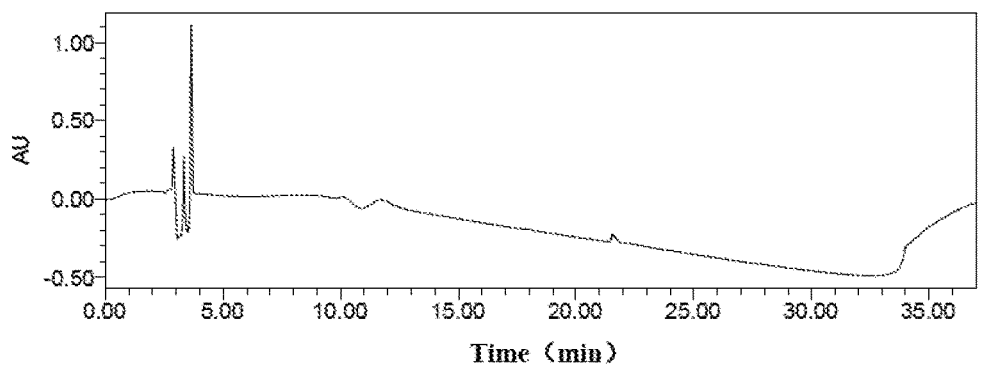
FIG. 5B is HPLC (210 nm peak) of methanol used to dissolve the compound dieselolein T6-6 in the control (no have biosurfactant in this sample).
Figure 6:
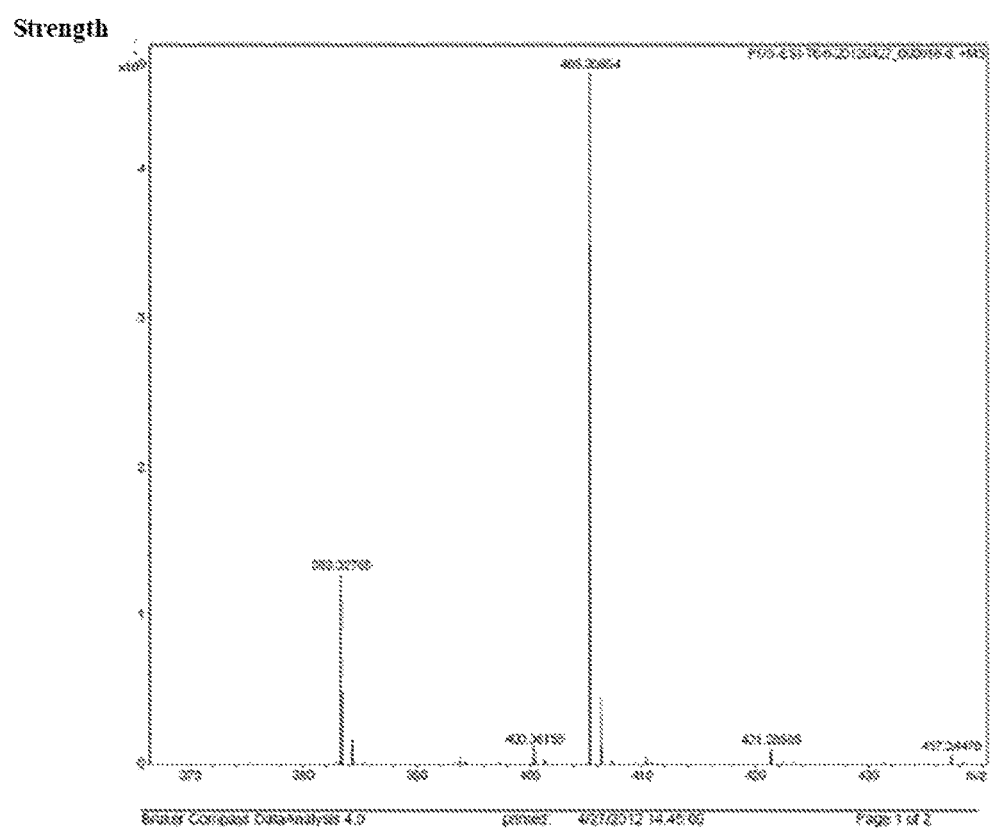
FIG. 6 is molecular mass spectra of the compound of dieselolein T6-6

Combine the organic phase (27.8 mNm-1) after extracting hydrophobic layer of Strain *Alcanivorax dieselolei* T6-6 and the organic phase (28.1 mNm-1) after sediment, freeze-drying and extraction of supernatant acid of *Alcanivorax dieselolei* T6-6, and make acidic ninhydrin coloration after running TLC plate. Compared with iodine coloration, most material is lipopeptide. Then use HPLC to detect polar size of active substance. HPLC results and TLC running results are used to determine eluting solvent passing through normal phase silica gel column and its eluting gradient. The subsequent isolation and purification process of target active substance is getting through the normal phase silica gel column first and then reversed phase silica gel column, and finally gel column to further purify and prepare isolated samples. The ratio for the eluent getting through normal phase column is 100%/o chloroform, followed by chloroform:methanol=50:1, chloroform:methanol=10:1, chloroform:methanol=4:1, and 100% methanol. The elution volume varies with amount of samples, and is always 2-3 column volumes. After getting through normal phase column for two times, non-basic lipopeptide substances can be removed. Use HPLC to detect size of polarity and range of absorption peak of lipopeptides components. Set conditions for getting through the reversed-phase column based on HPLC results. The reversed phase column adopts AKTA Purifier 10 connecting the reverse phase column. There are two detection wavelengths of 210 nm and 254 nm with continuous gradient elution (0-100% methanol at continuous gradient, at a flow rate of 10 ml/min). After continuously washing for 30 minutes with 100% methanol, wash the sample with pure acetonitrile for 40 minutes. According to elution order, there are 8 components; the seventh peak is 3.02 AU in height with duration of about 4.5 minutes, and the eluting gradient is 92%-93% methanol. The first peak of the first component is 4.5 AU in height with duration of about 2.5 minutes, and the eluting gradient is about 5% methanol. Surface tensions of the two components with higher peak are detected, and the results show that No. 1 component does not decrease its surface tension, while No. 7 component has a better surface activity. The surface tension of water decreases from 78.6 to 32.3 after adding 300 ul unconcentrated surfactant to 20 ml DDW; No. 7 component is purified by HPLC, and the results show the purity is so high that it is unnecessary to get through gel column. Layer expansion agents at different polarities are used to detect purity of final samples, with 100% chloroform, chloroform:methanol=3:1, chloroform:methanol=2:1, chloroform:methanol=1:1 and 100% methanol respectively used as expansion layer of expansion layer agent. Iodine coloration shows a single point, so the substances are dried to hit nuclear magnetism. During the whole process of isolation, chemical coloration and activity detection are considered as tracking indexes. The strains with high surface activity should be further isolated. Active substance produced by *Alcanivorax dieselolei* T6-6 after fermentation should get through positive column for two times; after collecting component sample, the expanded layer should be colored with iodine vapor and ninhydrin, and iodine coloration results of TLC layer expansion (FIG. 4A) and ninhydrin coloration results (FIG. 4B) are shown. Coloration results show that surfactant is so pure after getting through positive column for two times, and just few impurities with high polarity move to edge of layer expansion agent, so that No. 7 and No. 8 should be merged together. Combined surfactant should be detected by HPLC. The chromatogram of HPLC column for surfactant extracted from fermentation liquid of *Alcanivorax dieselolei* T6-6 are shown in FIG. 3. FIG. 5A is the figure of active substances merged by T6-6 running HPLC (wavelength of peak is 210 mm). and, FIG. 5B is the methanol control (wavelength of peak is 210 mm). In both figures, the solvent peak is found 5 minutes ago, and the peak of active substances is found at the point of 18 minutes in FIG. 5A.

Example 6: Structural Characterization of the Biosurfactant Produced by Hydrocarbon-Degrading Bacterium *Alcanivorax dieselolei* T6-6 the molecular weight of biosurfactant was determined by FT-MS (obtained in the example 5)

The results obtained by an FT-MS (Fourier transform ion cyclotron resonance mass spectrometer) indicate that molecular ion peaks are [M+H] of 383.32765, [M+Na] of 405.30854 and [M+Kcl] of 421.28506, while theoretical [M+H] and [M+Na] are 383.3268 and 405.3088 respectively, errors of an actual numerical value and a theoretical value are 2.2 ppm and 0.6 ppm respectively, and generally, experimental error smaller than 5 ppm is considered tolerable. Therefore, theoretical molecular weight of lipopeptide produced by the strain *Alcanivorax dieselolei* T6-6 is 382.32.

According to comparison results of a high-resolution mass spectrum analyzer, the substance only contains C, H, O and N, and its molecular weight is 382.32 on the basis of results of mass spectrum 6. After comparison, only one molecular formula $C_{22}H_{42}N_2O_3$ is possible within an error range smaller than 5 ppm, which is completely identical with the molecular formula deduced by the NMR. Refer to Table 4 for the analysis result.

TABLE 4 the FT-MS Analysis Table of strain *Alcanivorax dieselolei* T6-6 produced biosurfactants (hexadecane as the sole carbon source)

| Lipopeptides | Molecular Weight |
| --- | --- |
| [M + H]$^+$ | 383.32765 |
| [M + Na]$^+$ | 405.30854 |
| [M + Kcl]$^+$ | 421.28506 |

(b) NMR Spectra Analysis

The chemical formula $C_{22}H_{42}N_2O_3$ of the lipopeptide produced by the strain *Alcanivorax dieselolei* T6-6 is further proved by the analysis results of the NMR spectrum. The fatty acid of the strain *Alcanivorax dieselolei* T6-6 is a hexadecanoic acid with beta-hydroxy, and the amino acid is lysine. Amino of lysine and carboxyl of hexadecanoic acid are dehydrated and condensed to obtain amide bonds, and the imino group of lysine and beta-hydroxy of hexadecanoic acid are reacted to obtain beta-lactam four-membered ring containing nitrogen. At present, no rings formed by independent amino acid and fatty acid in well-known cyclic lipopeptide surfactant are reported.

The substance has three polar groups including amido bonds, amino and carboxyl, with stronger polarity at the hydrophilic end. It can be seen from comparison that the lipopeptide is surfactant of novel structure.

Figure 7:
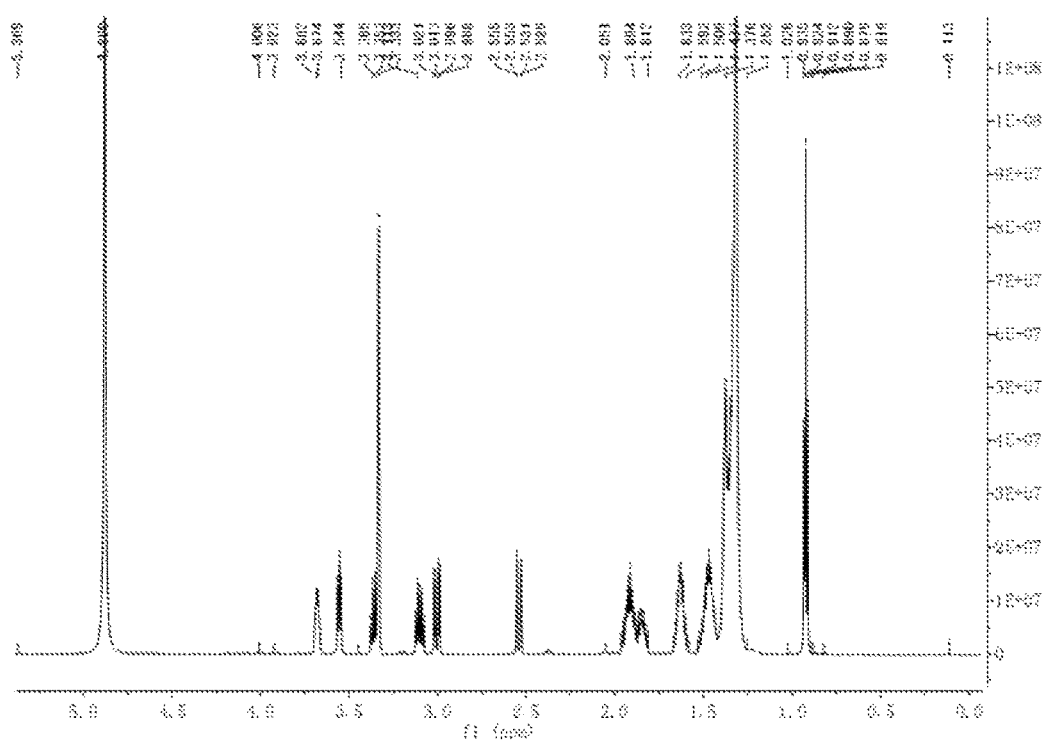
FIG. 7 is $^1$H-NMR spectra of purified compound from dieselolein T6-6
Figure 8:
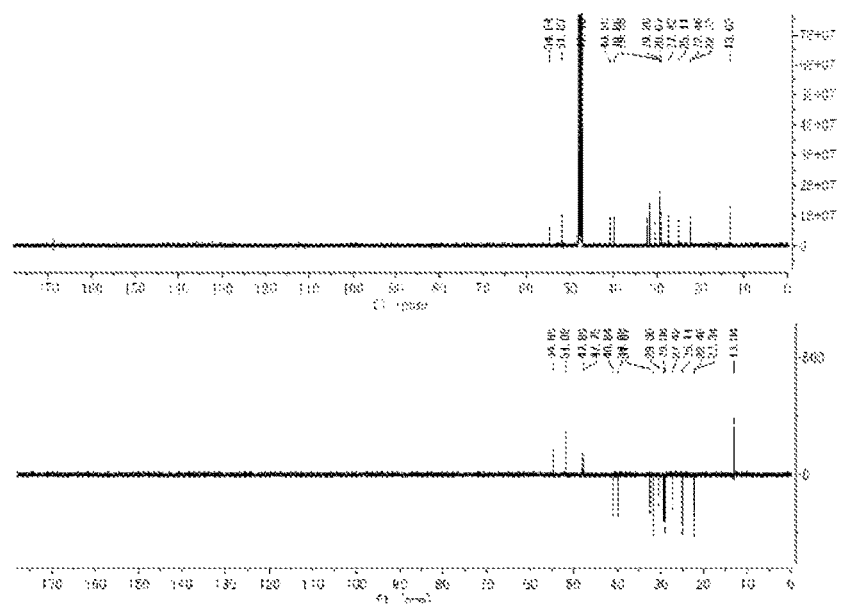
FIG. 8 is $^{13}$C-NMR spectra of purified compound from dieselolein T6-6
Figure 9:
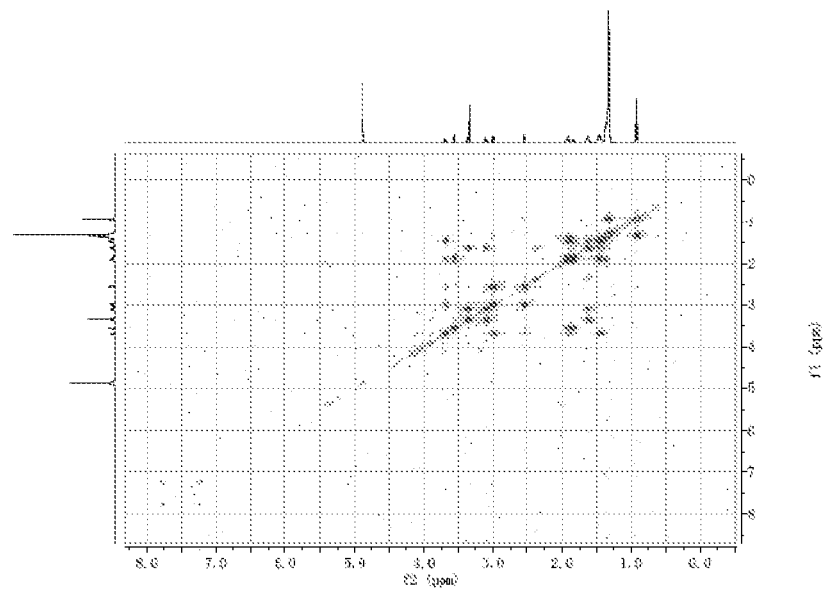
FIG. 9 is $^1$H-1HCOSY spectra of purified compound from dieselolein T6-6
Figure 10:
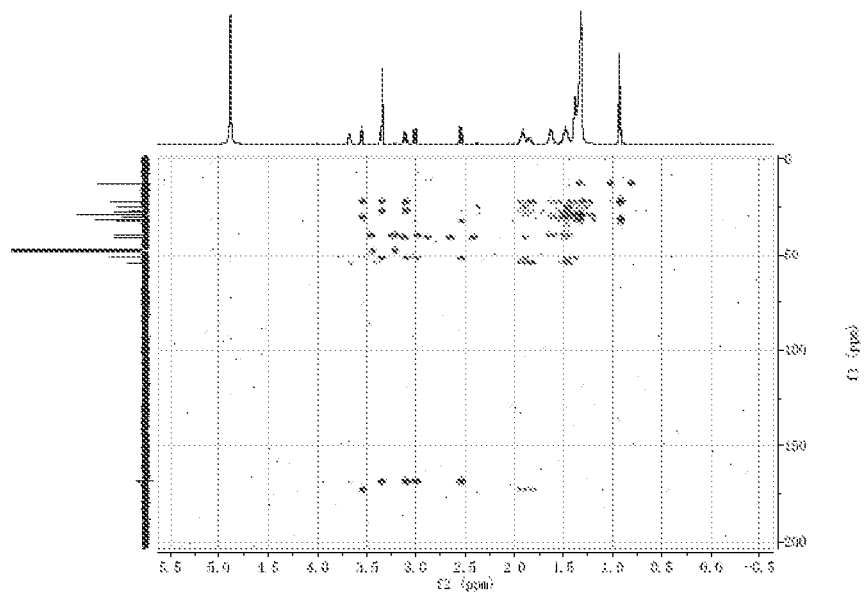
FIG. 10 is HMBC spectra of purified compound from dieselolein T6-6
Figure 11:
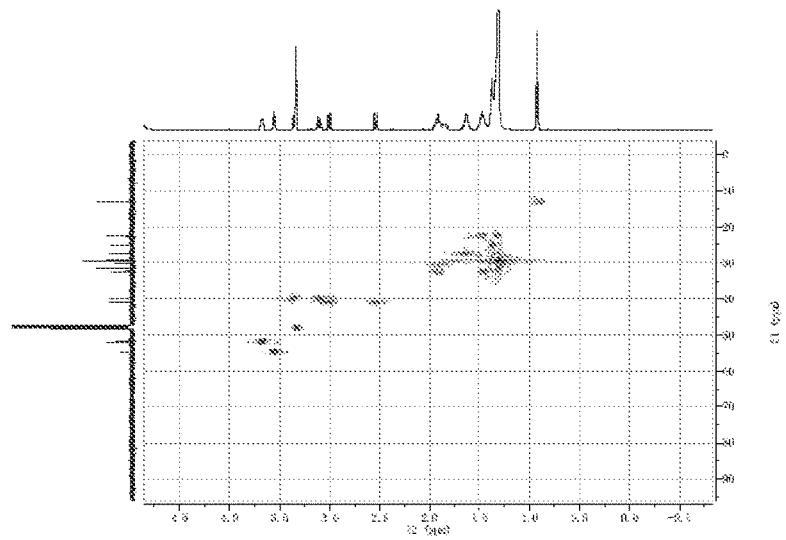
FIG. 11 is HMQC spectra of purified compound from dieselolein T6-6

FIG. 7 is a 1H-NMR spectrum of the pure Compound *dieselolei* T6-6, FIG. 8 is a 13C-NMR spectrum of the pure compound *dieselolei* T6-6 proton NMR spectral data of pure Compounds *dieselolei* T6-6:

$^1$H NMR (600 MHz, CD$_3$OD-d$_4$) $\delta_H$ 3.68 (2H, m, H-8), 3.55 (1H, t, J=6.0, Hz, H-2), 3.35 (1H, m, H-6a), 3.10 (1H, m, H-6b), 3.01 (1H, dd, J=4.8, 14.7 Hz, H-9a), 2.54 (1H, dd, J=1.2, 14.7 Hz, H-9b), 1.91 (1H, m, H-10a), 1.47 (1H, m, H-10b), 1.91 (1H, m, H-3a), 1.84 (1H, m, H-3b), 1.63 (2H, m, H-5), 1.47 (2H, m, H-4), 1.38 (2H, m, H-11), 1.32 (16H, m, H-12~19), 1.32 (2H, m, H-21), 1.31 (2H, m, H-20), 0.92 (3H, t, J=6.9 Hz, H-22)

carbon NMR spectral data of pure Compounds *dieselolei* T6-6:

$^{13}$C NMR (151 MHz, CD$_3$OD-d$_4$), $\delta_C$ 172.9 (C-1), 168.7 (C-7), 54.6 (C-2), 51.9 (C-8), 40.9 (C-9), 39.9 (C-6), 32.4 (C-10), 31.7 (C-20), 30.4 (C-3), 29.1~29.38 (C-12~19) 27.4 (C-5), 25.1 (C-11), 22.5 (C-4), 22.3 (C-21), 13.0 (C-22); ESIMS m/z 383.32765 [M+Na]$^+$ FIG. 9 is a 1H-1HCOSY spectrum of the pure Compound *dieselolei* T6-6. FIG. 10 is a HMBC spectrum of the pure Compound *dieselolei* T6-6. FIG. 11 is a 1H-1 HMQC spectrum of the pure Compound *dieselolei* T6-6.

Combined with data of the FT-MS and the NMR detained in FIGS. 7 to 11, the new compound produced by fermenting the strain *Alcanivorax dieselolei* T6-6 is structured as following:

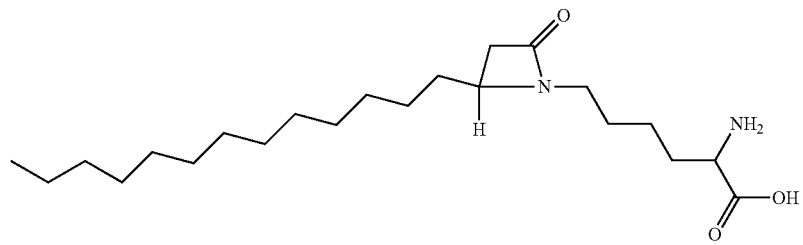 [SMILES: CCCCCCCCCCCCCC1CC(=O)N1CCCCC(N)C(=O)O]

Common Chinese of new compound named: *dieselolei* T6-6, Chinese system named: 2-amino-6-(N-2-carbonyl-4-tridecyl-cyclobutane) hexanoic acid, English named: 2-amino-6-(2-oxo-4-tridecyl-azetidine-1-yl) hexanoic acid, as a lysine resin.

When isolating by using the same method as above, subsequent isolation and purification process of the target active substance get through the normal phase silica gel column first and then the reversed phase silica gel column, and finally the gel column to prepare isolated samples after further purification. The ratio for getting through the normal phase column eluent is 100% chloroform, followed by chloroform:methanol=50:1, chloroform:methanol=10:1, chloroform:methanol=4:1, and 100% methanol. The elution volume varies with amount of samples, and is always 2-3 column volumes. After getting through the normal phase column for two times, non-basic lipopeptide substances can be removed. Use HPLC to detect the size of polarity and range of absorption peak of lipopeptides components. Set conditions for getting through the reversed-phase column based on HPLC results. The reverse phase column adopts AKTA Purifier 10 connecting the reverse phase column. There are two detection wavelengths of 210 nm and 254 nm with continuous gradient elution (0-100% methanol at continuous gradient, at a flow rate of 10 ml/min). Beginning with 0% methanol, substances with high polarity are eluted first, and then substances with poor polarity. Order of eluted materials are shown as the sequence of n=14 in the table below. After washing with 100% methanol for 30 minutes, the substances are washed with pure acetonitrile for 40 minutes. Structural formula of this compound is as follows:

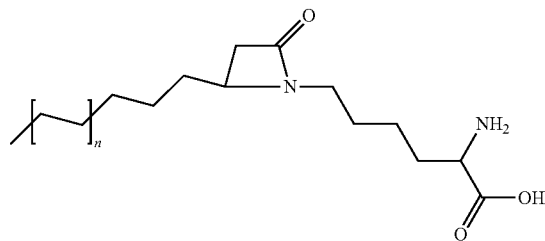

n = 1-4

TABLE 9 is elution conditions of the compounds

| Compound Name | Molecular Formula | Molecular Weight | n | Elution gradi- entrang- ing from |
|---|---|---|---|---|
| 2-Amino--6-(N-2-carbonyl-4-nonyl-azetidine-1-yl)hexanoic acid | C$_{18}$H$_{34}$N$_2$O$_3$ | 326 | n = 1 | 70%-78% methanol |

TABLE 9-continued is elution conditions of the compounds

| Compound Name | Molecular Formula | Molecular Weight | n | Elution gradi- entrang- ing from |
|---|---|---|---|---|
| 2-Amino--6-(N-2-carbonyl-4-undecyl-azetidine-1-yl) hexanoic acid | C$_{20}$H$_{38}$N$_2$O$_3$ | 354 | n = 2 | 80%-88% methanol |
| 2-amino-6-(2-oxo-4-tridecyl-azetidine-1-yl)hexanoic acid | C$_{22}$H$_{42}$N$_2$O$_3$ | 382 | n = 3 | 92%-93% methanol |
| 2-Amino--6-(N-2-carbonyl-4-pentadecyl-azetidine-1-yl) hexanoic acid | C$_{24}$H$_{46}$N$_2$O$_3$ | 410 | n = 4 | More than 94% of methanol |

Embodiment 7: Determination of Physicochemical Properties of Lipopeptide Surfactant Produced by Strain *Alcanivorax dieselolei* T6-6

In order to understand physicochemical properties and functions of biosurfactants produced by strain *Alcanivorax dieselolei* T6-6 (also called *dieselolei* T6-6) after fermentation, we determined CMC value and MAD value of purified lysine ester (i.e. *dieselolei* T6-6), and also determined the size of oil expansion ring of lysine ester at different temperatures and pH values to verify the stability of biosurfactant, as well as its emulsification effect on different organisms.

Determination method of biosurfactant CMC values: prepare different concentrations of water solution from pure biosurfactants to be determined, and measure its surface tension with surface tension meter. With the increase of surface activity (concentration), the surface tension of water solution gradually increases. The surface tension stops decreasing when the concentration increases to a certain level. The amount of surfactant corresponding to this critical surface tension is CMC value. The results are shown in Table 5.

TABLE 5 is a comparison of CMC values of several biosurfactant with expanding oil test

| biosurfactant | CMC (mg/l) |
| --- | --- |
| lysine lipid produced by strains *Alcanivorax dieselolei* T6-6 | 32 |
| Rhamnolipid | 50 |
| Surfactin | 45 |
| SDS | 23 |

Determination method of biosurfactant MAD (Minimum Active Dose) values: prepare different concentrations of water solution from pure biosurfactants to be determined, and measure the oil expansion activity through oil expansion experiment. With the decrease of concentration, the oil expansion ability of water solution becomes weaker and weaker, and completely disappears when the concentration decreases to a certain level. The amount of surfactant at the time of oil expansion ability disappearing is the MAD value. The results are shown in Table 6.

MAD values in Table 6 Table expanding oil experimental comparison of several surfactants

| biosurfactant | MAD (µg) |
| --- | --- |
| lysine lipid produced by strains *Alcanivorax dieselolei* T6-6 | 0.105 ± 0.05 |
| Tween 20 | 0.3 ± 0.07 |
| Tween 80 | 0.15 ± 0.05 |
| Triton X-100 | 0.3 ± 0.08 |
| SDS | 6.0 ± 0.12 |

"±" indicates three experimental error

Figure 12:
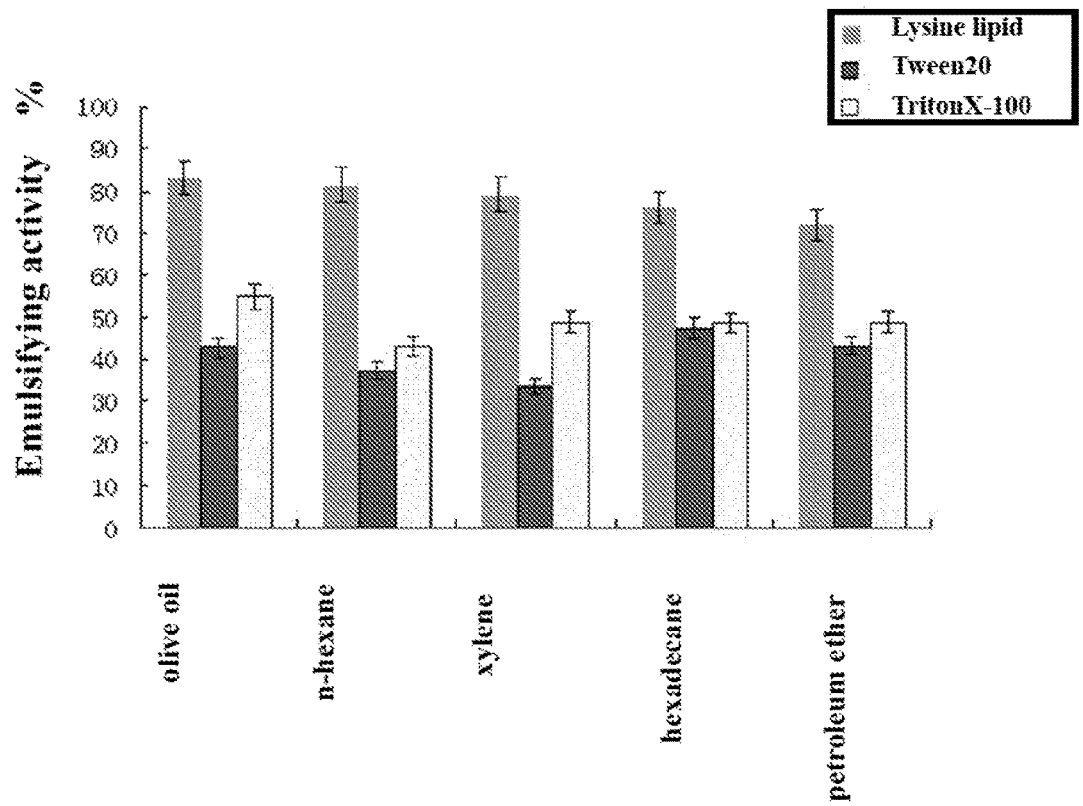
FIG. 12 is Comparison of emulsifying activity of lysine lipid produced by T6-6 and synthetic surfactants Tween 20 and Triton X-100

In order to understand the emulsifying activity of lysine ester produced by strain *Alcanivorax dieselolei* T6-6, we determined the emulsifying stability value of lysine ester produced by strain *Alcanivorax dieselolei* T6-6 and the chemical surfactants Tween 20 and Triton X-100 against olive oil, n-hexane, dimethylbenzene, hexadecane and petroleum ether. Determination method of biosurfactant emulsifying property: add 5 ml commercially available diesel No. 0 and 5 ml surfactant solution (1%) into a test tube, treat it with ultrasonic generator at 800 W for 40 s, and measure the emulsion and oil phase at different times (0 to 24 hours). Emulsion stable value (Es %)=emulsified layer height (cm)/oil phase height (cm)×100. Specific results are shown in FIG. 12. The emulsifying activity test result of lysine ester produced by strain *Alcanivorax dieselolei* T6-6 indicates that it has a higher emulsifying activity than chemical surfactant Tween 20 and Triton X-100. Lysine ester produced by strains *Alcanivorax dieselolei* T6-6 has a good emulsifying activity (83±1%) on olive oil, and can maintain 48 h at room temperature. Its emulsifying activity on four other organics is also more than 75%. Good emulsifying activity makes it greatly valuable in environmental pollution control.

Figure 13:
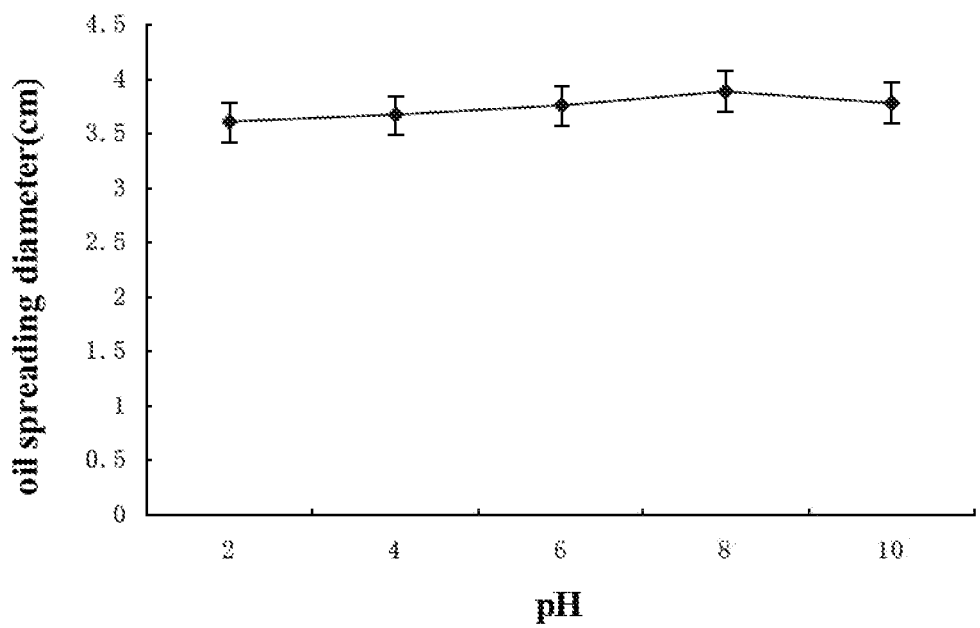
FIG. 13 is Effects of pH on the surface activity of the biosurfactant of T6-6.
Figure 14:
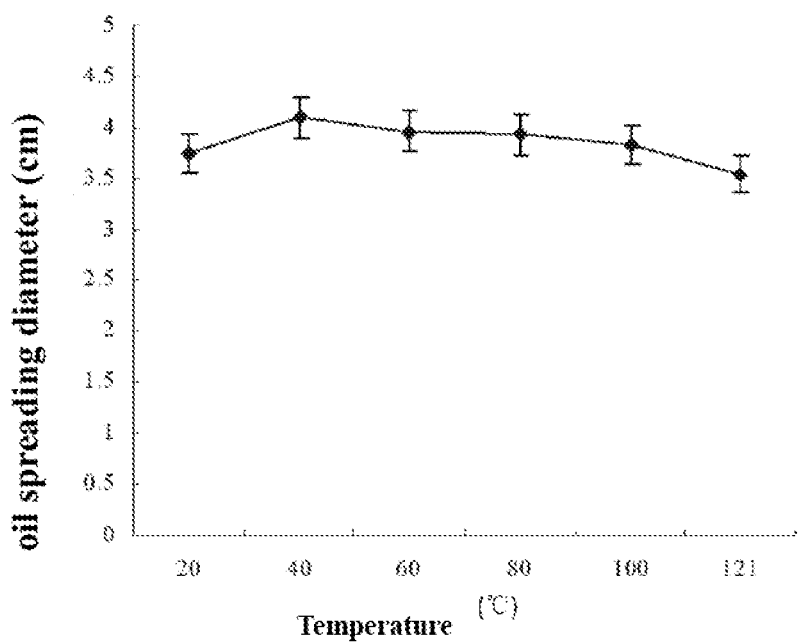
FIG. 14 is Effects of temperature on the surface activity of the biosurfactant of T6-6.

Activity test of lysine ester produced by strain *Alcanivorax dieselolei* T6-6 at different temperatures and pH values (oil expansion experiment) shows that it has a good thermal stability and pH tolerance, as shown in FIGS. 13 and 14. Determination method of biosurfactant oil expansion activity: Take a culture dish, add water, and add 0.1 ml hexadecane on the water surface to form oil film. Add the fermentation liquid from the shake flask to the center of oil film to make the central film squeezed to form a circle, the diameter of which positively correlates to the concentration and activity of the biosurfactant. Strains with cycle diameter more than 3 cm are retained for further study. Set pH value in the range of 2 to 10 to determine effect of pH on lysine ester produced by the strain *Alcanivorax dieselolei* T6-6. Oil expansion diameter varies from 3.6 to 3.9 for lysine ester produced by the strain *Alcanivorax dieselolei* T6-6 with small fluctuation. It has a good acid and base resistance, and the activity is the highest at pH=8. Considering the structure, it can be inferred that this material is alkaline. And also, when adding a few drops of ammonia expansion on the running TLC plate, the substance will expand more fully, which also proves that it is alkaline.

Treat the pure lysine ester produced by strain *Alcanivorax dieselolei* T6-6 at temperatures of 20° C., 40° C., 60° C., 80° C. and 100° C. for one hour, and then determine its activity. The results show that the oil expansion diameter is 3.7 to 4.1 cm, without significant change in the activity. After the sample was treated at high temperature of 121° C. for 15 minutes, the oil expansion diameter slightly decreases to about 3.5 cm, indicating a slight decrease of activity. Good thermal stability makes it possible for the substance to be used in high temperature fields.

Embodiment 8: Test of Cytotoxic Activity and Antimicrobial Activity of Lysine Ester Produced by Strain *Alcanivorax dieselolei* T6-6

Antibacterial activity test method: use filter paper method to detect antibacterial activity of biosurfactant produced by fermentation of strain *Alcanivorax dieselolei* T6-6. The indicator bacteria are Gram-negative bacteria, Gram-positive bacteria, endophytic pathogenic fungus in tea tree and yeasts. Specific steps: coat the well-shaken indicator bacteria on the culture plate, stick filter paper on each scribe region, and drip surfactant on filter paper. The control group is the methanol solvent of same amount. After bacteria are inverted cultured in constant temperature incubation at 28° C. for a certain period (different indicator bacteria have different growth cycles; bacteria grow quickly, but endophytic fungus in tea tree should grow 3-5 days), and observe the results to detect inhibition zone. If there is an inhibition zone, its size should be measured.

As indicated by bacteriostasis experiments, the active substances produced by the *Alcanivorax dieselolei* T6-6 have better antimicrobial activity against six strains of gram-positive bacteria like *bacillus*, two strains of plant pathogenic fungi and one strain of yeast but no suppression effect against the gram-positive bacteria such as *E. coli*. DH5 alpha, *aeromonas hydrophila* and *Campbell vibrio*.

The results are shown in Table 7.

| Indicator bacteria genus name | Inhibition zone (mm) |
|---|---|
| *Lysinibacillus sphaericus* | 11.7 |
| *Ornithinibacillus bavariensis* | 14.2 |
| *Bacillus plakortidis* | 13.7 |
| *Bacillus thuringiensis* | 7.2 |
| *Bacillus rhizosphaerae* | 10.4 |
| *Bacillus safensis* | 10.9 |
| *Phomaexigua* var. *exigua* | 16.3 |
| *Pestalotiopsistheae* | 10.19 |
| *Rhodotorula mucilaginosa* | 12.1 |

Cytotoxic activity test method: measure cytotoxic activity using a Cell Counting Kit-8 (CCK-8 kit for short and of Dojindo Laboratories, Japan), namely, a human CCK (cholecystokinin) octapeptide ELISA (enzyme-linked immunosorbent assay) kit. The human CCK octapeptide ELISA is a quick high-sensitivity detection kit based on WST-8 and widely applied to cell proliferation and cytotoxic activity.

WST-8 is a compound similar to the MTT. With the presence of electronic coupling reagent, WST-8 can be reduced by some dehydrogenases in mitochondria and produce orange formazan. The more and faster the cell proliferation is, the deeper the color; the greater the cytotoxicity is, the lighter the color. For the same cells, the color depth has a linear relationship with the number of cells. Solvent DMSO is used in control group, and pure lysine ester produced by strain *Alcanivorax dieselolei* T6-6 dissolved in DMSO are used in experimental group. Cells are hepatoma cells 7402 and normal hepatocytes 7702 (available from Sino-US Joint Venture Biohermes Biomedical Technology Ltd). Medicinal concentration is 100 ug/ml, and operation is taken according to kit instruction, with each step repeated three times. After medication, $OD_{600}$ is detected in cellular fluid after culturing for 48 hours. Cell toxicity results are shown in Table 8:

| The results in Table 8 Table Cytotoxicity | | |
|---|---|---|
| | Determination of cell culture fluid $OD_{600}$ | |
| Samples of different treatments | Hepatoma cells 7402 | Normal liver cells 7702 |
| DMSO | 1.667 | 0.863 |
| lysine lipid produced by strains *Alcanivorax dieselolei* T6-6 | 0.121 | 0.282 |

The medicine-to-cell suppression rate=[negative group (DMSO)−experimental group (dosed)]/negative group (DMSO). Data in Table 8 are substituted into the formula to work out the suppression rate (92.74% for hepatoma carcinoma cells 7402 and 67.32% for normal hepatocyte cells 7702) of the active substances of lysine ester produced by the strain *Alcanivorax dieselolei* T6-6. Accordingly, the active substances of lysine ester generated by the strain *Alcanivorax dieselolei* T6-6 have better cytotoxic activity.

Although the above has shown and described the embodiments of present invention, it is understood that the above embodiments are exemplary and are not to be construed as the limitation of this invention. General technician in the field can change, modify, substitute and vary above embodiments within the scope of inventory without departing from the principles and spirit of the invention.

SEQUENCE LISTING

<160> NUMBER OF SEQ ID NOS: 3

<210> SEQ ID NO 1
<211> LENGTH: 1510
<212> TYPE: DNA
<213> ORGANISM: Alcanivorax dieseloleiT6-6

<400> SEQUENCE: 1

```
gatcagagtt tgatcctggc tcagattgaa cgctggcggc aggcctaaca catgcaagtc      60
gagcggaaac gatgggagct tgctcccagg cgtcgagcgg cggacgggtg agtaacacgt     120
gggaatctgc ccattagtgg gggataactc ggggaaactc gagctaatac cgcataatcc     180
ctacggggga aagcagggga tcttcggacc ttgcgctgat ggatgagccc gcgtcggatt     240
agcttgttgg tggggtaatg gcccaccaag gcgacgatcc gtaactggtc tgagaggatg     300
gccagtcaca ccgggactga gacacggccc ggactcctac gggaggcagc agtggggaat     360
cttggacaat gggcgcaagc ctgatccagc catgccgcgt gtgtgaagaa ggccttcggg     420
ttgtaaagca ctttcagtag ggaggaaggc tttgggctaa tacctggag tacttgacgt      480 tacctacaga agaagcaccg gctaatttcg tgccagcagc cgcggtaata cgaaaggtgc     540
gagcgttaat cggaattact gggcgtaaag cgcgcgtagg cggtgtgtta agtcggatgt     600
gaaagcccag ggctcaacct tggaattgca tccgatactg gcacgctaga gtgcagtaga     660
gggaggtgga atttccggtg tagcggtgaa atgcgtagag atcggaagga acaccagtgg     720
cgaaggcggc ctcctggact gacactgacg ctgaggtgcg aaagcgtggg gagcaaacag     780
gattagatac cctggtagtc cacgccgtaa acgatgtcta ctagccgttg ggtccttag      840
```

```
tgactttggt ggcgcagcta acgcgataag tagaccgcct ggggagtacg gccgcaaggt    900
taaaactcaa atgaattgac gggggcccgc acaagcggtg gagcatgtgg tttaattcga    960
tgcaacgcga agaaccttac caggccttga catcctgcga actttctaga gatagattgg   1020
tgccttcggg agcgcagtga caggtgctgc atggctgtcg tcagctcgtg tcgtgagatg   1080
ttgggttaag tcccgtaacg agcgcaaccc ttgtccttag ttgccagcac ttcgggtggg   1140
aactctaggg agactgccgg tgacaaaccg gaggaaggtg gggacgacgt caagtcatca   1200
tggcccttac ggcctgggct acacacgtgc tacaatggtt ggtacagagg gttgcgaagt   1260
cgcgaggcgg agctaatctc tcaaagccaa tcgtagtccg gattggagtc tgcaactcga   1320
ctccatgaag tcggaatcgc tagtaatcgc ggatcagaat gccgcggtga atacgttccc   1380
gggccttgta cacaccgccc gtcacaccat gggagtggga tgcaccagaa gtagttagtc   1440
taaccttcgg gaggacgatt accacggtgt ggttcatgac tggggtgaag tcgtaacaag   1500
gtagccgtaa                                                         1510

<210> SEQ ID NO 2
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: The sources of the genetic material are
      Alcanivoraxdieselolei T6-6 and Alcanivorax dieseloleiB-5.

<400> SEQUENCE: 2
agagtttgat cctggctcag                                                20

<210> SEQ ID NO 3
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: The sources of the genetic material are
      Alcanivoraxdieselolei T6-6 and Alcanivorax dieseloleiB-5.

<400> SEQUENCE: 3
acggctacct tgttacgact                                                20
```

wherein when n=4, a molecular formula of the compound is $C_{24}H_{46}N_2O_3$, a molecular weight is 410, the compound is named as 2-amino-6-(N-2-carbonyl-4-pentadecyl-cyclobutane) hexanoic acid.
2. The compound of claim 1, wherein the compound is lysine aliphatic *dieselolei* T6-6 which has the structural formula:
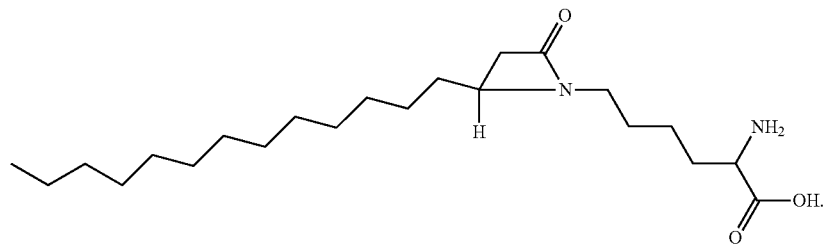 [SMILES: CCCCCCCCCCCCCC1CC(=O)N1CCCCC(N)C(=O)O]

What is claimed is:

1. A compound, wherein, the compound is produced by a fermentation of bacterium *Alcanivorax dieselolei* T6-6, accession number: CGMCC NO: 9033;

wherein a structural formula of the compound is:

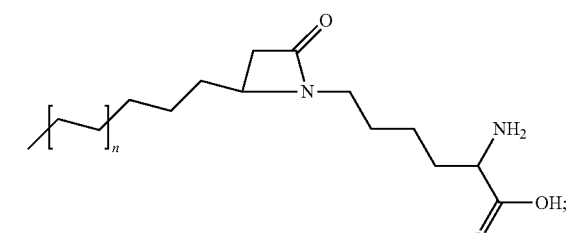

n = 1-4 wherein when n=1, a molecular formula of the compound is $C_{18}H_{34}N_2O_3$, a molecular weight is 326, the compound is named as 2-amino-6-(N-2-carbonyl-4-nonyl-cyclobutane) hexanoic acid;

wherein when n=2, a molecular formula of the compound is $C_{20}H_{38}N_2O_3$, a molecular weight is 354, the compound is named as 2-amino-6-(N-2-carbonyl-4-undecyl-cyclobutane) hexanoic acid;

wherein when n=3, a molecular formula of the compound is $C_{22}H_{42}N_2O_3$, a molecular weight is 382, the compound is named as 2-Amino-6-(N-2-carbonyl-4-tridecyl-cyclobutane) hexanoic acid or lysine aliphatic *dieselolei* T6-6;